US009878321B2

(12) United States Patent
Kamionka et al.

(10) Patent No.: US 9,878,321 B2
(45) Date of Patent: Jan. 30, 2018

(54) MATERIALS AND METHODS FOR THE SELECTIVE RECOVERY OF MULTIVALENT PRODUCTS

(71) Applicant: INVISTA North America S.a.r.l., Wilmington, DE (US)

(72) Inventors: Mariusz Kamionka, Wilmington, DE (US); Alex Conradie, Eaglescliffe (GB)

(73) Assignee: INVISTA NORTH AMERICA S.Á.R.L., Wilmington, DE (US)

( * ) Notice: Subject to any disclaimer, the term of this patent is extended or adjusted under 35 U.S.C. 154(b) by 0 days.

(21) Appl. No.: 15/094,930

(22) Filed: Apr. 8, 2016

(65) Prior Publication Data

US 2016/0296926 A1    Oct. 13, 2016

Related U.S. Application Data

(60) Provisional application No. 62/144,884, filed on Apr. 8, 2015.

(51) Int. Cl.
| | | |
|---|---|---|
| C07C 209/86 | (2006.01) | |
| B01J 47/04 | (2006.01) | |
| C01F 1/00 | (2006.01) | |
| B01J 47/00 | (2017.01) | |
| C02F 1/42 | (2006.01) | |
| B01J 39/18 | (2017.01) | |
| B01J 47/014 | (2017.01) | |
| B01J 47/11 | (2017.01) | |
| B01J 49/05 | (2017.01) | |
| C02F 1/20 | (2006.01) | |
| C02F 101/34 | (2006.01) | |
| C02F 101/38 | (2006.01) | |

(52) U.S. Cl.
CPC ............ *B01J 47/003* (2013.01); *B01J 39/18* (2013.01); *B01J 47/014* (2017.01); *B01J 47/11* (2017.01); *B01J 49/05* (2017.01); *C02F 1/42* (2013.01); *C07C 209/86* (2013.01); *C02F 1/20* (2013.01); *C02F 2101/34* (2013.01); *C02F 2101/38* (2013.01); *C02F 2303/16* (2013.01)

(58) Field of Classification Search
None
See application file for complete search history.

(56) References Cited

U.S. PATENT DOCUMENTS

| | | |
|---|---|---|
| 3,393,233 A | 7/1968 | Richter et al. |
| 6,284,904 B1 | 9/2001 | Ponnampalam |
| 2012/0289742 A1* | 11/2012 | Gerberding ............ C07C 51/43 562/580 |

FOREIGN PATENT DOCUMENTS

WO    WO 90/08730    8/1990

OTHER PUBLICATIONS

International Search Report and Written Opinion for PCT.US2016/026754, issued from European Patent Office dated Jun. 17, 2016 (13 pages).

* cited by examiner

*Primary Examiner* — Clinton Brooks
(74) *Attorney, Agent, or Firm* — William J. Simmons; Mark Feldstein (57) ABSTRACT

Described herein are processes and apparatus for the high purity and high concentration recovery of multivalent products via continuous ion exchange from aqueous solutions for further down-stream purification.

10 Claims, 5 Drawing Sheets

| | Unit | Hexamethylene-diamine | Lysine | Glutamate | 3-hydroxybutyrate | Pyruvate |
|---|---|---|---|---|---|---|
| Feed purity | [%] (w/w) | 77.4 | 3.0 | 6.4 | 4.4 | 8.8 |
| Adsorption loading | [g/(L resin)] | 103.1 | 2.4* | 1.2 | -1.0* | 0 |
| Post monovalent adsorption loading | [g/(L resin)] | 139.8 | 0.7 | 0.5 | | |
| Concentrating fold increase | [-] | 1.36 | 0.3 | | | |
| Elution purity | [%] (w/w) | 99.2 | 0.5 | 0.3 | | |

* Mass balance closure across the unit operation not within ±10 [%].

FIG. 4

| | Unit | Hexamethylene-diamine | Lysine | Glutamate | 3-hydroxybutyrate | Pyruvate |
|---|---|---|---|---|---|---|
| Feed purity | [%] (w/w) | 88.1 | 1.6 | 2.4 | 3.4 | 4.6 |
| Adsorption loading | [g/(L resin)] | 155.6 | 1.2 | 0.1 | -2.7* | -0.4 |
| Post monovalent adsorption loading | [g/(L resin)] | 214.6 | 0.7 | | | |
| Concentrating fold increase | [-] | 1.38 | 0.6 | | | |
| Elution purity | [%] (w/w) | 99.6 | 0.4 | | | |

* Mass balance closure across the unit operation not within ±10 [%].

MATERIALS AND METHODS FOR THE SELECTIVE RECOVERY OF MULTIVALENT PRODUCTS

TECHNICAL FIELD

The present disclosure relates to materials and methods for the selective recovery of one or more multivalent product. The present disclosure relates to methods for the selective recovery of a multivalent product from an aqueous solution using, for example, continuous ion exchange. In combination with an ammonia/ammonium carbonate stripper, the materials and methods of the present disclosure produce a high purity, high concentration intermediate product stream for further purification, lowering the cost of the overall downstream processing.

SUMMARY

Multivalent products, i.e. molecules that exhibit more than one valence, require high concentration recovery from aqueous solutions at high purity for further purification. For example, the amino acid L-arginine is largely divalent at pH~1 and largely monovalent at pH~4. L-arginine may be produced via fermentation into an aqueous medium, which includes inorganic ionic species and organic by-products, e.g. monovalent amino acids, as competitive species in adsorption processes such as ion exchange. Such monovalent by-products compete for adsorption sites at a pH~4, resulting in a lower purity, high concentration, intermediate stream for purification. Recovery of divalent L-arginine at pH~1 allows rejection of monovalent by-products from the ion exchange resin producing a high purity product, but reduces the concentration of the intermediate stream for purification.

Many other multivalent products produced into an aqueous medium require high purity and high concentration recovery prior to further economical purification. Such multivalent products include, but are not limited to, (1) dicarboxylic acids such as succinic acid, glutaric acid, adipic acid, pimelic acid and (2) diamines such as putrescine, cadaverine, hexamethylenediamine, heptamethylenediamine. Accordingly, against this background, it is clear that there is a need for methods underpinning the economic recovery of such multivalent products from aqueous solutions.

Recovery methods for purification of multivalent products can be implemented by a variety of different separation techniques. A non-limiting example includes optimizing the binding capacity of the charged compound via ion exchange. Ion exchange may involve at least one stage of adsorption, elution, and regeneration and in some applications, may include several regeneration and washing phases. "Batch mode" involves applying a mixture to a single column and applying various eluents in succession to improve adsorption of the target compound to the ion exchange resin. After the adsorption step, the ion exchange resin can be regenerated with the appropriate eluent to repeat the process in a cyclical manner that does not attain steady state. Batch mode systems may be simple to use but can be impractical for large-scale industrial processes. Continuous ion exchange may allow for simultaneous adsorption and regeneration steps and thus, be more efficient since there is an automated, continuous staging of the recovery process that attains steady state operation. And, given the trade-off between producing a high purity product at high concentration without significant recovery loss, continuous ion exchange offers an alternative approach achieving both aims for multivalent products.

Accordingly, the present disclosure relates to materials and methods of recovering multivalent products at high purity and high concentration from an aqueous solution via continuous ion exchange using either cationic or anionic ion exchange adsorbents.

In at least one embodiment, the present disclosure provides for an apparatus comprising a continuous ion exchange carousel comprising a number of columns grouped into zones, for example, (1) a Dilute Adsorption Zone, (2) an Adsorption Zone, (3) an Adsorption Wash Zone, (4) a Back-Wash Zone, (5) a Monovalent Strip Zone, (6) a Monovalent Adsorption Zone, (7) an Elution Zone and (8) an Elution Wash Zone.

In one aspect, the disclosed methods provide for the recovery of a multivalent product from an aqueous solution, feeding an unclarified or clarified solution to the continuous ion exchange unit operation, principally adsorbing the multivalent product as the divalent specie in the Adsorption Zone and Dilute Adsorption Zone.

In another aspect, the disclosed methods selectively desorb monovalent by-products from the adsorbent and modifies the valence of the multivalent product from divalent to monovalent in the Monovalent Strip Zone.

In another aspect, the continuous ion exchange unit operation provides for concentrating re-adsorbing of the principally monovalent specie of the multivalent product on the ion exchange adsorbent in the Monovalent Adsorption Zone, fed from an ammonia/ammonium carbonate steam stripper unit operation.

In another aspect, the Monovalent Strip Zone and the Monovalent Adsorption Zone are combined; where the principally zero valence specie of the multivalent product, fed from an ammonia/ammonium carbonate stripper unit operation, both selectively desorbs monovalent by-products from the adsorbent and modifies the valence of the multivalent product from the divalent to the monovalent providing for concentrating re-adsorption onto the adsorbent.

In one aspect, the methods provide for the recovery of the multivalent product via elution from the ion exchange adsorbent using an ammonia, ammonium bicarbonate or ammonium carbonate solution as an eluent. Free ammonia and carbon dioxide are stripped from the eluate using a steam stripper.

In yet another aspect, the present disclosure relates to a bio-derived product, bio-based product or fermentation-derived product, wherein said product is obtained from process disclosed herein, and comprises:

i. a composition comprising at least one bio-derived, bio-based or fermentation-derived compound according to any one of processes disclosed herein, or any one of FIGS. 1-4 or any combination thereof, ii. a bio-derived, bio-based or fermentation-derived polymer comprising the bio-derived, bio-based or fermentation-derived composition or compound of i., or any combination thereof, iii. a bio-derived, bio-based or fermentation-derived resin comprising the bio-derived, bio-based or fermentation-derived compound or bio-derived, bio-based or fermentation-derived composition of i. or any combination thereof or the bio-derived, bio-based or fermentation-derived polymer of ii. or any combination thereof, iv. a molded substance obtained by molding the bio-derived, bio-based or fermentation-derived polymer of ii. or the bio-derived, bio-based or fermentation-derived resin of iii., or any combination thereof, v. a bio-derived, bio-based or fermentation-derived formulation comprising the bio-derived, bio-based or fermentation-derived composition of i., bio-derived, bio-based or fermentation-derived compound of i., bio-derived, bio-based or fermentation-derived polymer of ii., bio-derived, bio-based or fermentation-derived resin of iii., or bio-derived, bio-based or fermentation-derived molded substance of iv, or any combination thereof, or vi. a bio-derived, bio-based or fermentation-derived semi-solid or anon-semi-solid stream, comprising the bio-derived, bio-based or fermentation-derived composition of i., bio-derived, bio-based or fermentation-derived compound of i., bio-derived, bio-based or fermentation-derived polymer of ii., bio-derived, bio-based or fermentation-derived resin of iii., bio-derived, bio-based or fermentation-derived formulation of v., or bio-derived, bio-based or fermentation-derived molded substance of iv., or any combination thereof.

Unless otherwise defined, all technical and scientific terms used herein have the same meaning as commonly understood by one of ordinary skill in the art to which this disclosure pertains. Although methods and materials similar or equivalent to those described herein can be used to practice the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the present disclosure are set forth in the accompanying drawings and the description below. Other features, objects, and advantages of the present disclosure will be apparent from the description and drawings, and from the claims. The word "comprising" in the claims may be replaced by "consisting essentially of" or with "consisting of," according to standard practice in patent law.

DETAILED DESCRIPTION

Before the present embodiments are described, it is to be understood that the present disclosure is not limited to the particular apparatus, adsorbents, zones, methodologies or protocols described, as these may vary. It is also to be understood that the terminology used in the description is for the purpose of describing the particular versions or embodiments only, and is not intended to limit the scope of the present disclosure.

In general, this document provides, according to certain embodiments, for a continuous ion exchange unit operation, divided into a number of operating zones, producing a multivalent product for further purification. Such multivalent products include, but are not limited to; amino acids such as L-arginine; dicarboxylic acids such as, succinic acid, glutaric acid, adipic acid, pimelic acid and diamines such as putrescine, cadaverine, hexamethylenediamine and heptamethylenediamine, all of which are referred to as multivalent products herein. As used herein, the term "divalent" is used to denote a charged specie having either a 2+ or 2− valence. The term "monovalent" is used herein to denote a charged specie having either a 1+ or 1− valence. The term "first equivalence point" is used herein to denote the multivalent product's species distribution at $pH=0.5 \cdot (pK_{a1}+pK_{a2})$, where $pK_{a1}$ and $pK_{a2}$ are the first two acid dissociation constants for the multivalent product.

As used herein, the terms "unclarified" refers to a solution containing solid particulates such as cells or precipitates and "clarified" solutions are understood to mean a solution from which solid particulates have been removed.

As used herein, "adsorption zone" is understood to mean a stage in the recovery method comprising at least one column where the process stream containing the multivalent product to be recovered is added to a particular adsorbent resin and adsorbs to the adsorbent resin.

"Elution zone," as used herein, is understood to mean a stage in the recovery method where the multivalent product adsorbed to the adsorbent resin is desorbed into the liquid phase.

As used herein, "monovalent strip zone" is understood to mean a stage in the recovery method, where monovalent by-products are desorbed from the adsorbent and the valence of the multivalent product is changed from divalent to monovalent. The term "monovalent adsorption zone" is understood to mean a stage in the recovery method comprising at least one column where the majority of multivalent product adsorbed is the monovalent specie.

The terms "about" and "approximately," when used in connection with a specific value, means that acceptable deviations from that value are also encompassed but still provide substantially the same function as the specific value. Selective Adsorption and Particulate Removal A clarified or unclarified aqueous solution is pH adjusted to approximately the $pK_{a1}$ for cationic divalent products and to approximately the $pK_{a2}$ for anionic divalent products and fed to the Adsorption Zone (see e.g., STREAM 4, FIG. 1A and FIG. 1B), fed counter-current to the flow of the adsorbent phase.

The flow-through from the Adsorption Zone (see e.g., STREAM 3, FIG. 1A and FIG. 1B) is combined with the flow-through from the Adsorption Wash Zone (see e.g., STREAM 5, FIG. 1A and FIG. 1B) into an adsorption hold-up vessel, subsequently fed to the Dilute Adsorption Zone (see e.g., STREAM 2, FIG. 1A and FIG. 1B). The Adsorption Zone and Dilute Adsorption Zone facilitate adsorption of the multivalent product in principally the divalent state onto the adsorbent phase, competing for adsorption sites with other charged inorganic and organic species in the aqueous medium. The adsorbent flow rate is set to allows for minimal or zero break-through of the multivalent product into the adsorption effluent (see e.g., STREAM 1, FIG. 1A and FIG. 1B), whilst allowing for flow through of inorganic and organic charged and uncharged/zero valence species to waste treatment.

The adsorbent and interstitial hold-up in the Adsorption Zone (see e.g., COL POS: 13, FIG. 1A and FIG. 1B) moves into the Adsorption Wash Zone. Water fed into the Adsorption Wash Zone (see e.g., COL POS: 15, FIG. 1A and FIG. 1B) flushes the interstitial hold-up from the Adsorption Zone into the adsorption hold-up vessel, ensuring that no multivalent product, held interstitially, is carried forward into the Back-wash Zone.

Figure 1A:
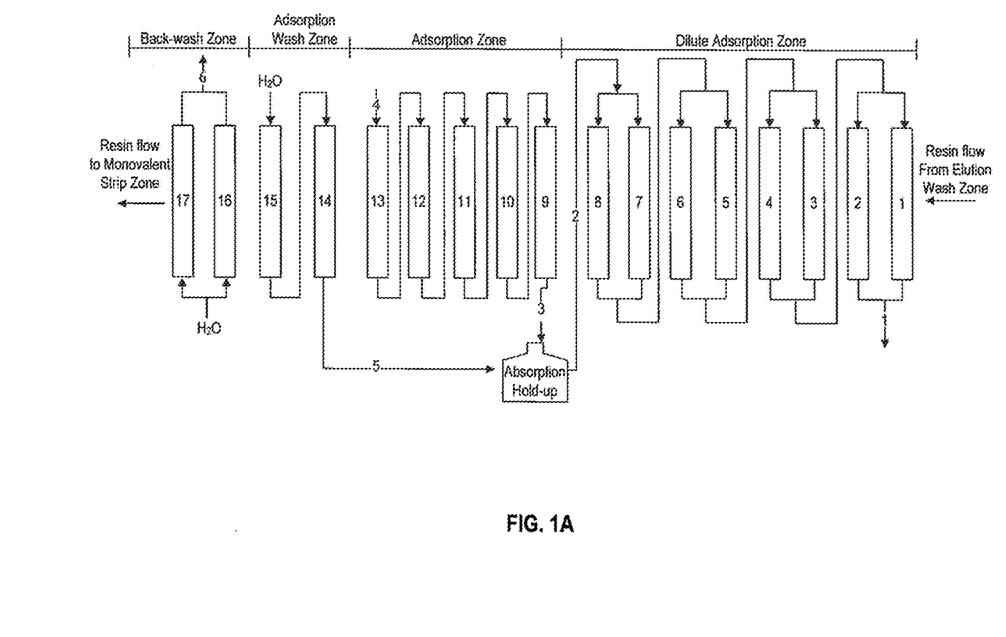
FIG. 1A and FIG. 1B are a schematic of an exemplary continuous ion exchange unit operation containing a separate Monovalent Strip Zone and a separate Monovalent Adsorption Zone, leading to the high purity and high concentration recovery of multivalent products prior to further purification.
Figure 1B:
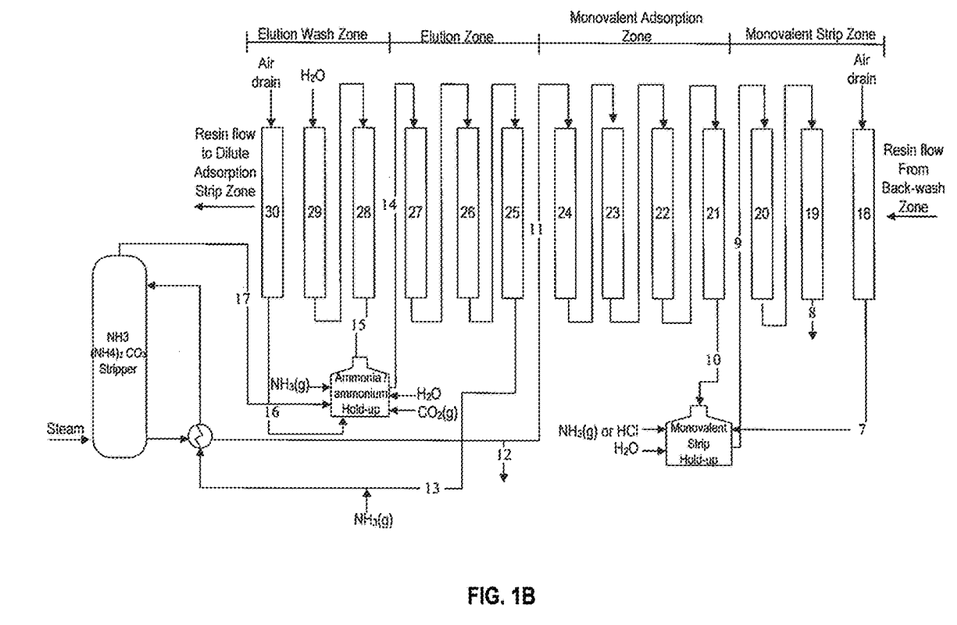

The Back-wash Zone fluidises the resin beds (see e.g., COL POS: 16 & 17), providing for entrained particulate removal from the resin beds (see e.g., STREAM 6, FIG. 1A and FIG. 1B).

Increasing Purity and Concentration of Adsorbed Multivalent Product Using a Separate Monovalent Strip Zone and a Separate Monovalent Adsorption Zone The adsorbed multivalent product moves from the Back-wash Zone (see e.g., COL POS: 17, FIG. 1A and FIG. 1B) into the Monovalent Strip Zone (see e.g., COL POS: 18, FIG. 1A and FIG. 1B). An air drain (see e.g., COL POS: 18, FIG. 1A and FIG. 1B), recovers the interstitial water hold-up carried forward from the Back-wash Zone into the monovalent strip hold-up vessel (see e.g., STREAM 7, FIG. 1A and FIG. 1B).

The monovalent strip hold-up vessel is charged with a base such as $NH_3(g)$ or an acid such as HCl or $H_2SO_4$ at a concentration that allows for the effluent pH from the Monovalent Strip Zone (see e.g., STREAM 8, FIG. 1A and FIG. 1B) to be approximately the $pK_{a2}$ for cationic divalent products and approximately the $pK_{a1}$ for anionic divalent products. The Monovalent Strip Zone is fed from the Monovalent strip hold-up vessel (see e.g., STREAM 9, FIG. 1A and FIG. 1B), desorbing adsorbed species that are uncharged or having zero valence between the pH of the monovalent strip hold-up vessel and the first equivalence point. Consequently, the multivalent product is converted from the principally divalent to the largely monovalent state, freeing adsorption sites for use in the Monovalent Adsorption Zone. The flow through from the Monovalent Strip Zone is diverted to waste water treatment (see e.g. STREAM 8, FIG. 1A and FIG. 1B).

Ammonia/ammonium carbonate steam stripping (see FIG. 1A and FIG. 1B) to approximately the first equivalence point, produces a multivalent product that has a principally monovalent valence species distribution. The Monovalent Adsorption Zone is fed from the ammonia/ammonium carbonate stripper (see e.g., STREAM 11, FIG. 1A and FIG. 1B), providing for adsorption of the monovalent specie of the multivalent product onto the free adsorbent sites, thereby increasing the concentration of the multivalent product adsorbed to the adsorbent phase. The Monovalent Adsorption Zone feed rate is set to allow for minimal or zero break-through of the multivalent product into the flow through (see e.g., STREAM 10, FIG. 1A and FIG. 1B). The flow through (see e.g., STREAM 10, FIG. 1A and FIG. 1B) from the Monovalent Adsorption Zone is recovered into the monovalent strip holdup vessel.

The adsorbed monovalent specie of the multivalent product moves from the Monovalent Adsorption Zone (see e.g., COL POS: 24, FIG. 1A and FIG. 1B) into the Elution Zone (see e.g., COL POS: 25, FIG. 1A and FIG. 1B). The Elution Zone is fed from a high concentration ammonia/ammonium hold-up vessel (see e.g., STREAM 14, FIG. 1A and FIG. 1B), eluting all multivalent product from the adsorbent. The eluate (see e.g., STREAM 13, FIG. 1A and FIG. 1B) is fed to the ammonia/ammonium carbonate stripper, recovering free ammonia and carbon dioxide as feed to the concentration ammonia/ammonium hold-up vessel (see e.g., STREAM 17, FIG. 1A and FIG. 1B).

The regenerated resin moves from the Elution Zone (see e.g., COL POS: 27, FIG. 1A and FIG. 1B) into the Elution Wash Zone (see e.g., COL POS: 28, FIG. 1A and FIG. 1B). An aqueous solution, for example, water, is fed into the Elution Wash Zone (see e.g., COL POS: 29, FIG. 1A and FIG. 1B) and flushes interstitial ammonia/ammonium (bi) carbonate into the concentrated ammonia/ammonium hold-up vessel (see e.g. STREAM 15, FIG. 1A and FIG. 1B). Finally, the interstitial water is recovered via an air drain (see e.g., COL POS: 30, FIG. 1A and FIG. 1B) into the concentrated ammonia/ammonium hold-up (see e.g., STREAM 16, FIG. 1A and FIG. 1B).

The adsorbent moves from the Elution Wash Zone (see e.g., COL POS: 30, FIG. 1A and FIG. 1B) into the Dilute Adsorption Zone (see e.g., COL POS: 1, FIG. 1A and FIG. 1B) and the adsorbent repeats the passage through the various carousel zones as described above.

STREAM 12 (see FIG. 1A and FIG. 1B) represents the net flow of multivalent product to further down-stream processing.

Figure 2A:
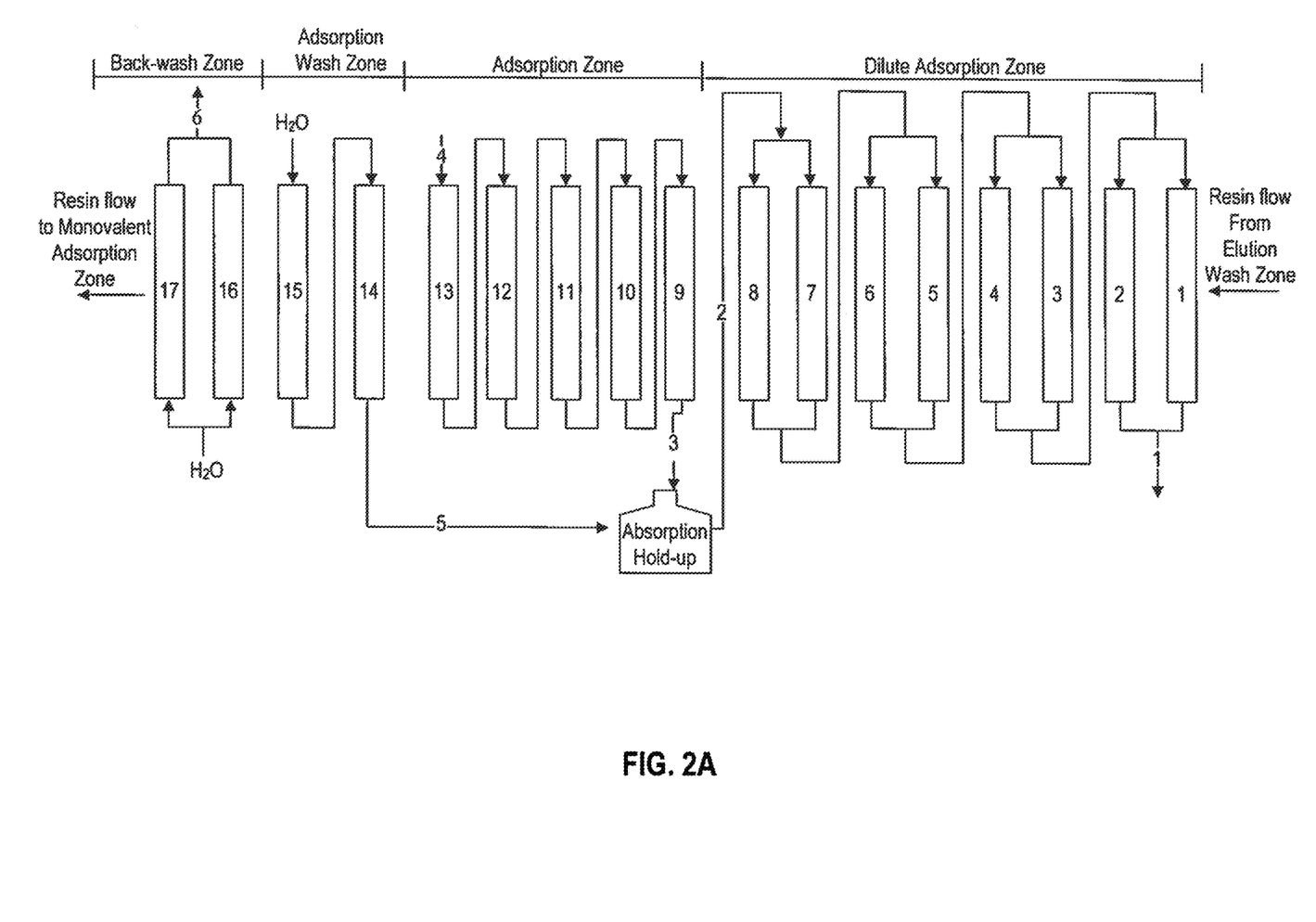
FIG. 2A and FIG. 2B are a schematic of an exemplary continuous ion exchange unit operation containing a combined Monovalent Strip Zone and a Monovalent Adsorption Zone, leading to the high purity and high concentration recovery of multivalent products prior to further purification.
Figure 2B:
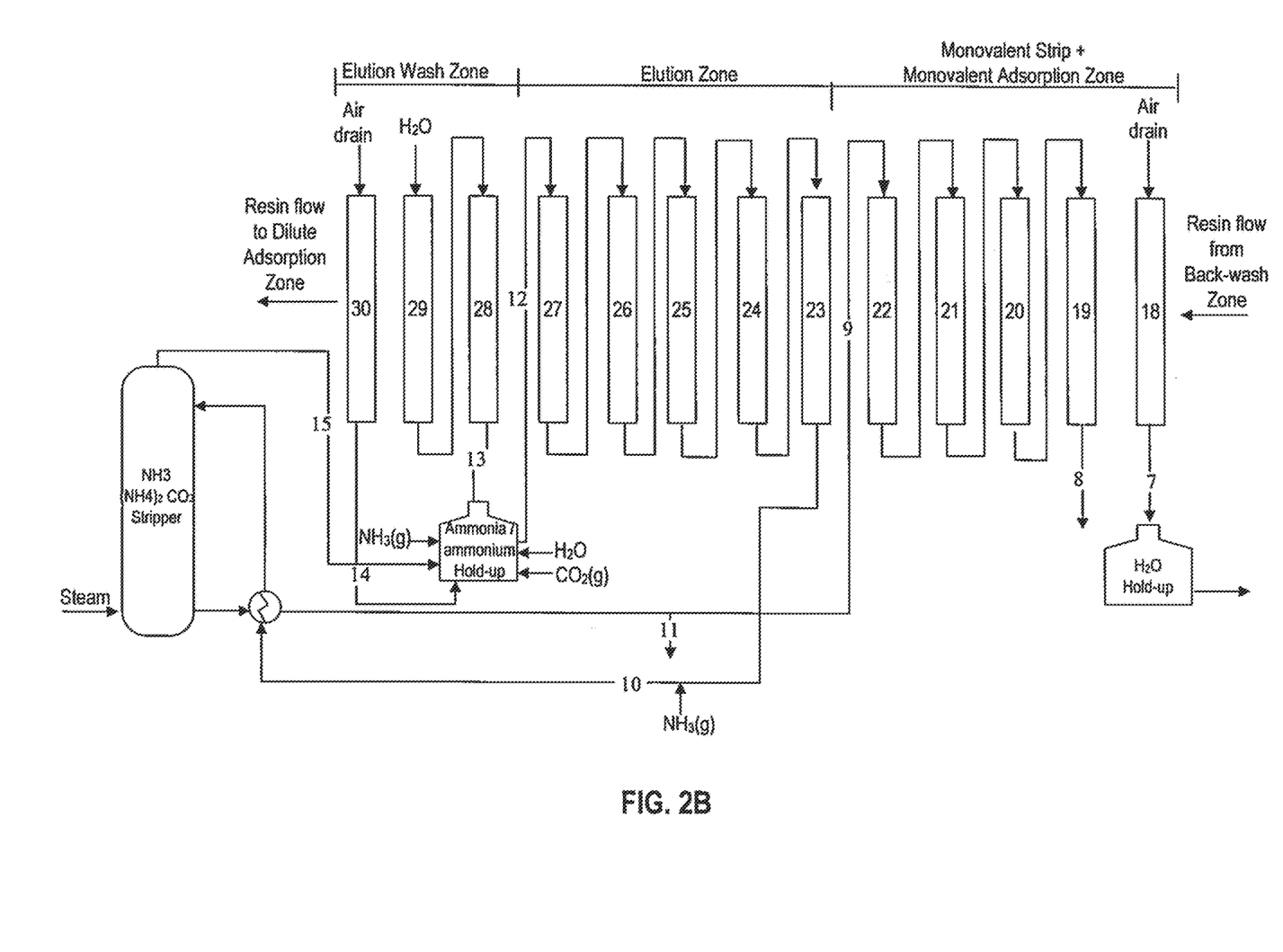

Increasing Purity and Concentration of Adsorbed Multivalent Product Using a Combined Monovalent Strip Zone and Monovalent Adsorption Zone The adsorbed multivalent product moves from the Back-wash Zone (see e.g., COL POS: 17, FIG. 2A and FIG. 2B) into the combined Monovalent Strip and Adsorption Zone (see e.g., COL POS: 18, FIG. 2A and FIG. 2B). An air drain (see e.g., COL POS: 18, FIG. 2A and FIG. 2B), recovers the interstitial water hold-up carried forward from the Back-wash Zone into a water recovery hold-up vessel (see e.g., STREAM 7, FIG. 2A and FIG. 2B).

Ammonia/ammonium carbonate steam stripping (see FIG. 2A and FIG. 2B) to a pH where the multivalent product has a principally zero valence species distribution is fed to the combined Monovalent Strip and Adsorption Zone (see e.g., STREAM 9, FIG. 2A and FIG. 2B), desorbing adsorbed species that are uncharged or having zero valence between the feed (see e.g., STREAM 9, FIG. 2A and FIG. 2B) and effluent pH (see e.g., STREAM 8, FIG. 2A and FIG. 2B). Consequently, the multivalent product adsorbed to the adsorbent is converted from the principally divalent to the largely monovalent state, freeing adsorption sites. Also, the zero valence multivalent product in the feed (see e.g., STREAM 9, FIG. 2A and FIG. 2B) is converted to the monovalent state and adsorbed onto the free adsorbent sites, thereby increasing the concentration of the multivalent product adsorbed to the adsorbent phase. The combined Monovalent Strip and Adsorption Zone feed rate is set to allow for minimal or zero break-through of the multivalent product into the flow through (see e.g., STREAM 8, FIG. 2A and FIG. 2B). The flow through (see e.g., STREAM 8, FIG. 2A and FIG. 2B) from the Monovalent Adsorption Zone is diverted to waste water treatment.

The adsorbed monovalent specie of the multivalent product moves from the combined Monovalent Strip and Adsorption Zone (see e.g., COL POS: 22, FIG. 2A and FIG. 2B) into the Elution Zone (see e.g., COL POS: 23, FIG. 2A and FIG. 2B). The Elution Zone is fed from a high concentration ammonia/ammonium hold-up vessel (see e.g., STREAM 12, FIG. 2A and FIG. 2B), eluting all multivalent product from the adsorbent. The eluate (see e.g., STREAM 10, FIG. 2A and FIG. 2B) is fed to the ammonia/ammonium carbonate stripper, recovering free ammonia and carbon dioxide as feed to the concentration ammonia/ammonium hold-up vessel (see e.g., STREAM 15, FIG. 2A and FIG. 2B).

The regenerated resin moves from the Elution Zone (see e.g., COL POS: 27, FIG. 2A and FIG. 2B) into the Elution Wash Zone (see e.g., COL POS: 28, FIG. 2A and FIG. 2B). An aqueous solution, for example, water, is fed into the Elution Wash Zone (see e.g., COL POS: 29, FIG. 2A and FIG. 2B) and flushes interstitial ammonia/ammonium (bi) carbonate into the concentrated ammonia/ammonium hold-up vessel (see e.g. STREAM 13, FIG. 2A and FIG. 2B). Finally, the interstitial water is recovered via an air drain (see e.g., COL POS: 30, FIG. 2A and FIG. 2B) into the concentrated ammonia/ammonium hold-up (see e.g., STREAM 14, FIG. 2A and FIG. 2B).

The adsorbent moves from the Elution Wash Zone (see e.g., COL POS: 30, FIG. 2A and FIG. 2B) into the Dilute Adsorption Zone (see e.g., COL POS: 1, FIG. 2A and FIG. 2B) and the adsorbent repeats the passage through the various carousel zones as described above.

STREAM 11 (see FIG. 1A and FIG. 1B) represents the net flow of multivalent product to further down-stream processing.

EXAMPLES

Example 1

Recovery of Hexamethylenediamine from a Synthetic Feed Representing Clarified Fermentation Broth Using Continuous Ion Exchange with Separate Monovalent Strip and Separate Monovalent Adsorption Zone A column with a diameter of 25.4 [mm] was packed to a free settled bed height of approximately 600 [mm] using virgin Dowex Monosphere 650C cationic exchange resin. The virgin resin was washed with purified water to remove solvents associated with its manufacture and converted to the $NH_4^+$ form using 10 [%] (w/w) $NH_3$(aq) and stored in purified water.

An Akta® Purifier was programmed to mimic the cyclical continuous adsorption sequence as contained in FIG. 1A and FIG. 1B for the purification of hexamethylenediamine (HMD) from a synthetic feed representing clarified fermentation broth. Accordingly, a synthetic solution having the feed purity as outlined in FIG. 3 was prepared as feed to the simulated Adsorption Zone, having an HMD concentration of approximately 35 [g/L]. The feed to the simulated Adsorption Wash Zone was comprised of purified water. The simulated Monovalent Strip Zone feed comprised a 1 [%] (w/w) $NH_3$(aq) solution. The feed from the ammonia/ammonium carbonate stripper to the simulated Monovalent Adsorption Zone comprised a HMD solution buffered with ammonium bicarbonate to pH=10.5 [-], having a final concentration of approximately 35 [g/L]. The simulated Elution Zone feed contained 2 [M] ammonium carbonate. The simulated Elution Wash Zone feed was comprised of purified water. Each Zone was fed with 3 bed volumes at a constant flow rate of 5 [mL/min].

Figure 3:
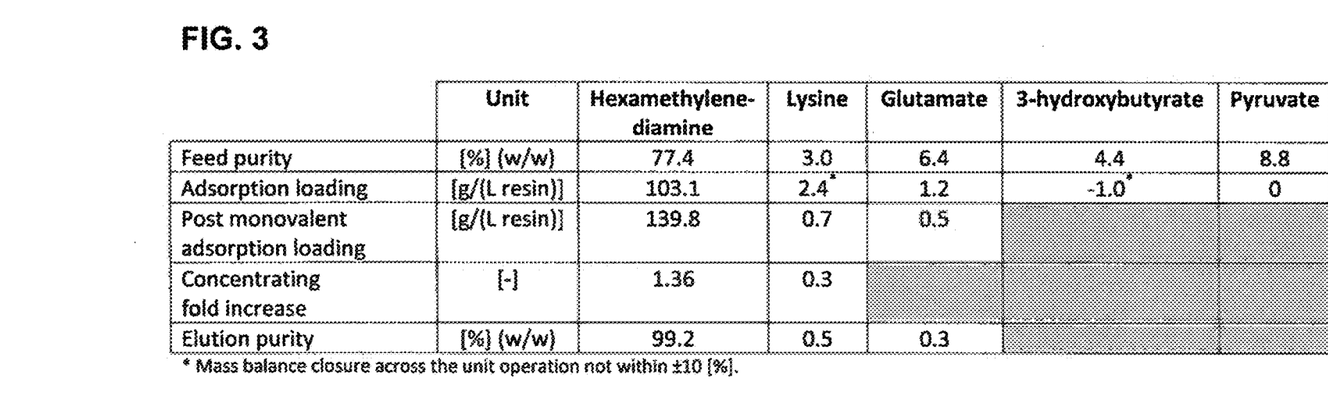
FIG. 3 tabulates the experimental results from an Akta® Purifier experiment programmed to mimic the cyclical continuous adsorption sequence as outlined in FIG. 1A and FIG. 1B.

FIG. 3 tabulates the results from the simulated cyclical continuous adsorption experiment. FIG. 3 demonstrates that the purity of the HMD was increased from 77.4 [%] (w/w) in the feed to 99.2 [%] in the eluate, the sequence having effectively rejected the four feed impurities down to trace quantities of lysine and glutamate. Also, the Monovalent Adsorption Zone concentrated the HMD product by a factor of 1.36. The results in FIG. 3 demonstrate that the continuous adsorption sequence outlined FIG. 1A and FIG. 1B both purifies and concentrates the desired product.

Example 2

Recovery of Hexamethylenediamine from a Synthetic Feed Representing Clarified Fermentation Broth Using Continuous Ion Exchange with a Combined Monovalent Strip and Monovalent Adsorption Zone A column with a diameter of 25.4 [mm] was packed to a free settled bed height of approximately 600 [mm] using virgin Dowex Monosphere 650C cationic exchange resin. The virgin resin was washed with purified water to remove solvents associated with its manufacture and converted to the $NH_4^+$ form using 10 [%] (w/w) $NH_3$(aq) and stored in purified water.

An Akta® Purifier was programmed to mimic the cyclical continuous adsorption sequence as contained in FIG. 2A and FIG. 2B for the purification of hexamethylenediamine (HMD) from a synthetic feed representing clarified fermentation broth. Accordingly, a synthetic solution having the feed purity as outlined in FIG. 4 was prepared as feed to the simulated Adsorption Zone, having an HMD concentration of approximately 54 [g/L]. The feed to the simulated Adsorption Wash Zone was comprised of purified water. The simulated combined Monovalent Strip and Adsorption Zone feed comprised a HMD solution in water, having a final concentration of approximately 54 [g/L]. The simulated Elution Zone feed contained 2 [M] ammonium carbonate. The simulated Elution Wash Zone feed was comprised of purified water. Each Zone was fed with 3 bed volumes at a constant flow rate of 5 [mL/min], barring the combined Monovalent Strip and Adsorption Zone which was fed with 2 bed volumes at a constant flow rate of 5 [mL/min].

Figure 4:
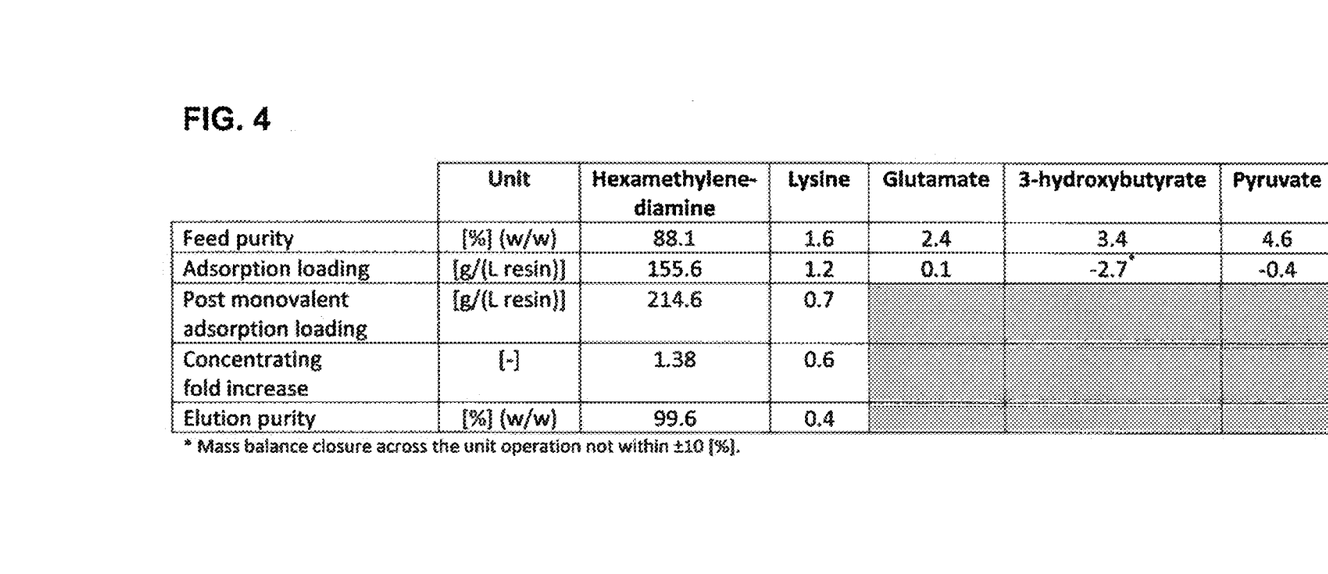
FIG. 4 tabulates the experimental results from an Akta® Purifier experiment programmed to mimic the cyclical continuous adsorption sequence as outlined in FIG. 2A and FIG. 2B.

FIG. 4 tabulates the results from the simulated cyclical continuous adsorption experiment. FIG. 4 demonstrates that the purity of the HMD was increased from 86 [%](w/w) in the feed to 99.6 [%] (w/w) in the eluate, the sequence having effectively rejected the four feed impurities down to trace quantities of lysine. Also, the combined Monovalent Strip and Adsorption Zone concentrated the HMD product by a factor of 1.38. The results in FIG. 4 demonstrate that the continuous adsorption sequence outlined in FIG. 2A and FIG. 2B both purifies and concentrates the desired product.

What is claimed is:

1. A method of recovering multivalent products from aqueous solutions using continuous ion exchange comprising:
   (a) adsorbing the multivalent product comprising diamine chosen from putrescine, cadaverine, hexamethylenediamine, and heptamethylenediamine, principally as a divalent species onto an ion exchange resin;
   (b) converting the adsorbed multivalent product to principally the monovalent valence state;
   (c) concentrating the multivalent product through re-adsorption onto the ion exchange resin; and
   (d) eluting the multivalent product.

2. The method of claim 1, wherein (1) impurities are selectively desorbed and (2) the adsorbed multivalent product is converted to principally the monovalent state by feeding a base or an acid at a concentration that allows the pH of the aqueous solution discharged from the resin to be approximately the $pK_{a2}$ for cationic divalent products and to be approximately the $pK_{a1}$ for anionic divalent products.

3. The method of claim 2, wherein the multivalent product at a pH of approximately a first equivalence point is recycled to the ion exchange resin and concentrated through re-adsorption.

4. The method of claim 1, wherein (1) impurities are selectively desorbed and (2) the adsorbed multivalent product is converted to principally the monovalent state by recycling the multivalent product in principally the zero valence state, concentrating the multivalent product though re-adsorption.

5. The method of claim 1, wherein the multivalent product is eluted from the ion exchange resin with ammonia, ammonium bicarbonate and/or ammonium carbonate.

6. The method of claim 3 or claim 5, where the eluted multivalent product is fed to a steam stripper, adjusting the pH of the multivalent product to approximately the first equivalence point.

7. The method of claim 4 or claim 5, where the eluted multivalent product is fed to a steam stripper, adjusting the pH of the multivalent product to where the multivalent product is principally in the zero valence state.

8. The method of claim 6, where a fraction of the multivalent product recovered from the steam stripper is recycled to the ion exchange resin and concentrated through re-adsorption.

9. The method of claim 1, further comprising at least one wash step after one or more of steps (a), (b), (c), and (d) using an aqueous solution.

10. The method of claim 7, where a fraction of the multivalent product recovered from the steam stripper is recycled to the ion exchange resin and concentrated through re-adsorption.

* * * * *